(12) United States Patent
Koblasz

(10) Patent No.: US 8,639,530 B2
(45) Date of Patent: Jan. 28, 2014

(54) MEDICATION ADVISORY SYSTEM

(75) Inventor: Arthur Koblasz, Atlanta, GA (US)

(73) Assignee: GT Angel, LLC, Atlanta, GA (US)

( * ) Notice: Subject to any disclaimer, the term of this patent is extended or adjusted under 35 U.S.C. 154(b) by 1556 days.

(21) Appl. No.: 11/712,126

(22) Filed: Feb. 27, 2007

(65) Prior Publication Data

US 2007/0203751 A1   Aug. 30, 2007

Related U.S. Application Data

(60) Provisional application No. 60/777,027, filed on Feb. 27, 2006.

(51) Int. Cl.
*G06Q 50/00* (2012.01)
(52) U.S. Cl.
USPC .................................................. 705/3; 705/2
(58) Field of Classification Search
USPC ......................................................... 705/2–3
See application file for complete search history.

(56) References Cited

U.S. PATENT DOCUMENTS

| | | | | |
|---|---|---|---|---|
| 3,921,318 A | | 11/1975 | Calavetta | |
| 5,301,105 A | * | 4/1994 | Cummings, Jr. | 705/2 |
| 5,471,382 A | * | 11/1995 | Tallman et al. | 600/300 |
| 5,499,293 A | * | 3/1996 | Behram et al. | 705/76 |
| 5,524,073 A | * | 6/1996 | Stambler | 705/75 |
| 5,666,492 A | * | 9/1997 | Rhodes et al. | 705/3 |
| 5,748,907 A | * | 5/1998 | Crane | 705/2 |
| 5,764,923 A | * | 6/1998 | Tallman et al. | 705/3 |
| 5,822,544 A | * | 10/1998 | Chaco et al. | 705/2 |
| 5,867,821 A | * | 2/1999 | Ballantyne et al. | 705/2 |
| 5,912,956 A | | 6/1999 | Longo et al. | |
| 2002/0060630 A1 | * | 5/2002 | Power | 340/573.1 |
| 2003/0149599 A1 | * | 8/2003 | Goodall et al. | 705/2 |
| 2005/0021519 A1 | | 1/2005 | Ghouri | |
| 2005/0121505 A1 | | 6/2005 | Metz et al. | |
| 2005/0187789 A1 | * | 8/2005 | Hatlestad et al. | 705/2 |
| 2005/0282566 A1 | * | 12/2005 | Bixler et al. | 455/466 |

\* cited by examiner

*Primary Examiner* — Sind Phongsvirajati
(74) *Attorney, Agent, or Firm* — Gardner Groff Greenwald & Villanueva, P.C.

(57) ABSTRACT

A medication information repository and analysis system receives prescription information indicating medication prescriptions filled for the patient, analyzes the prescription information to determine an estimate of recent medication consumption by the patient, and stores a medication advisory message indicating prescription and recent medication consumption information for the patient in association with a personal identifier assigned to the patient. A medication advisory delivery system automatically delivers the medication advisory message in response to a medication advisory request that is received in accordance with medication advisory contact information and indicates the personal identification number assigned to the patient. An emergency medical technician may issue the medication advisory request after reading a medication advisory tag carried by a patient identifying the medication advisory contact information and the personal identifier assigned to the patient.

20 Claims, 4 Drawing Sheets

MEDICATION ADVISORY SYSTEM

REFERENCE TO RELATED APPLICATION

This application claims filing priority to commonly owned U.S. Provisional Patent Application Ser. No. 60/777,027, entitled "New Devices for Preventing or Detecting Medication Errors" filed Feb. 27, 2006, which is incorporated herein by reference.

TECHNICAL FIELD

The present invention relates to medical information systems, and more particularly, to medication advisory tags and a related system for providing emergency medical technicians with medication advisory messages indicating a patient's prescription history, recent medication consumption, and other medical data.

BACKGROUND OF THE INVENTION

Millions of individuals require emergency medical care in the U.S. each year. These individuals sometimes need medical care in locations where medical information is not readily available to emergency care workers. The availability of such data often means the difference between life and serious injury or death. Recent medications, potentially dangerous allergies and prior diagnoses can be very important background information when emergency treatment is required.

Medical identification tags are well known in the related art and some of these medical advisory tags display a personal identification number (PIN) and website address (e.g. US2005/021519A1 to Ghouri). Other patents and publications describe medical advisory tags or cards which are electronic storage devices (e.g. US2005/0121505A1). Some electronic ID devices provide information at two levels, one level for emergency care and another level for long-term care. Most of these electronic tags or cards are very fragile and require a special electronic reader, such as a laptop computer or a PDA.

Another type of medical identification tag is described in U.S. Pat. No. 3,921,318 to Anthony wherein text and graphics are printed on microfilm attached to an ID card. The main drawbacks of this invention are that the microfilm is very fragile, and it is also very difficult to update medication information via microfilm when the patient's medications could be changing at monthly intervals. Will the card provider mail the individual a new ID card every month? This product would be very expensive if the card is expected to reveal accurate medication information.

Patent number U.S. Pat. No. 5,912,956 to Longo discloses a medical advisory tag with one or more telephone numbers printed on the tag revealing the tag wearer's home telephone number and other personal information. This invention also describes a different and more novel idea of dialing a specified telephone number, inputting additional numbers listed on the tag, and being automatically connected to a responsible person. No medical information is provided.

Despite the prior art of many different medical information systems, there are no information systems with accurate medication information that can be quickly accessed by a low-tech device like a cell phone or a "plain old telephone." When an ambulance arrives at a rescue scene, the emergency workers may not have a computer or time to read a website. Homecare nurses would have the same problem of not having access to a computer.

Most people are unable to remember all of their medications and dosages. Furthermore, it is common for elderly individuals to receive medical care from several different specialists, who may not communicate with each other about prescribed medications. The specialists sometimes rely on the patient to supply the medication information to other interested parties, which is a bad idea if a patient is experiencing an early stage of dementia.

Accordingly, there is a need for a cost effective and easy to use system for compiling, maintaining and providing accurate medication and medical history information to emergency healthcare providers.

SUMMARY OF THE INVENTION

The present invention meets the needs described above through a medication advisory system that receives, maintains and delivers automated medication information pertaining to a patient in response to an authorized request. The medication advisory system includes a medication information repository and analysis system that receives prescription information indicating medication prescriptions filled for the patient, analyzes the prescription information to determine an estimate of recent medication consumption by the patient, and stores a medication advisory message indicating prescription and recent medication consumption information for the patient in association with a personal identifier assigned to the patient. In particular, the medication advisory message may be stored as an organized text message or as a voice message recorded by a person with a clear voice. A medication advisory delivery system automatically delivers the medication advisory message in response to a medication advisory request that is received in accordance with medication advisory contact information which indicates the personal identification number assigned to the patient. For example, an emergency medical technician may issue the medication advisory request after reading a medication advisory tag carried by the patient identifying the medication advisory contact information and the personal identifier assigned to the patient.

The medication information repository is configured to serve as a centralized database of all medical prescriptions for a patient and may receive prescription information from multiple pharmacies that have filled prescriptions for the patient. This allows the repository to determine an estimate of recent medication consumption by the patient based on the prescription information received form the multiple pharmacies. The medication information repository may also receive additional medical information pertaining to the patient and include the additional medical information in the medication advisory message. For example, the additional medical information comprises medication allergy information pertaining to the patient. As another example, the medication information repository may receive medical insurance information pertaining to the patient and include the medical insurance information in the medication advisory message. The medication advisory delivery system may also use the insurance information to deliver a message to an insurance provider notifying the insurance provider that a medication advisory message has been delivered for the patient.

To ensure security of the patient's medication information, the medication advisory system is preferably configured to receive a requester identifier in association with the medication advisory request, and to determine whether the requester identifier is associated with a party authorized to receive the medication advisory message as a condition to delivering the medication advisory message. The medication information repository may also store a verification code in association with the personal identifier for the patient and include the verification code in the medication advisory message for the purpose of validating that a correct patient identifier has been included with the medication advisory request. As a further security measure, the medication information repository may store a patient photograph in association with the personal identifier for the patient and include the patient photograph in the medication advisory message for the purpose of validating that a correct patient is associated with the medication advisory message.

The medical advisory message may be delivered to an authorized requesting party in any appropriate manner. For example, the medication advisory system includes a telephone voice response unit, the medication advisory contact information includes a telephone directory number assigned to the telephone voice response unit, the medication advisory request includes a telephone call received by the telephone voice response unit, and the medication advisory message, includes a pre-recorded voice message. As another example, the medication advisory system include a text message response unit, the medication advisory contact information includes a text message access number assigned to the text message response unit, the medication advisory request includes a text message request received by the text message response unit, and the medication advisory message includes a text message response. In another alternative, the medication advisory system includes an Internet email server, the medication advisory contact information includes an Internet address assigned to the Internet email server, the medication advisory request includes an email received by the Internet email server, and the medication advisory message comprises an email response message.

It should also be understood that many other advantages and alternatives for practicing the invention will become apparent from the following detailed description of the preferred embodiments and the appended drawings.

DETAILED DESCRIPTION OF THE EMBODIMENTS

Figure 1:
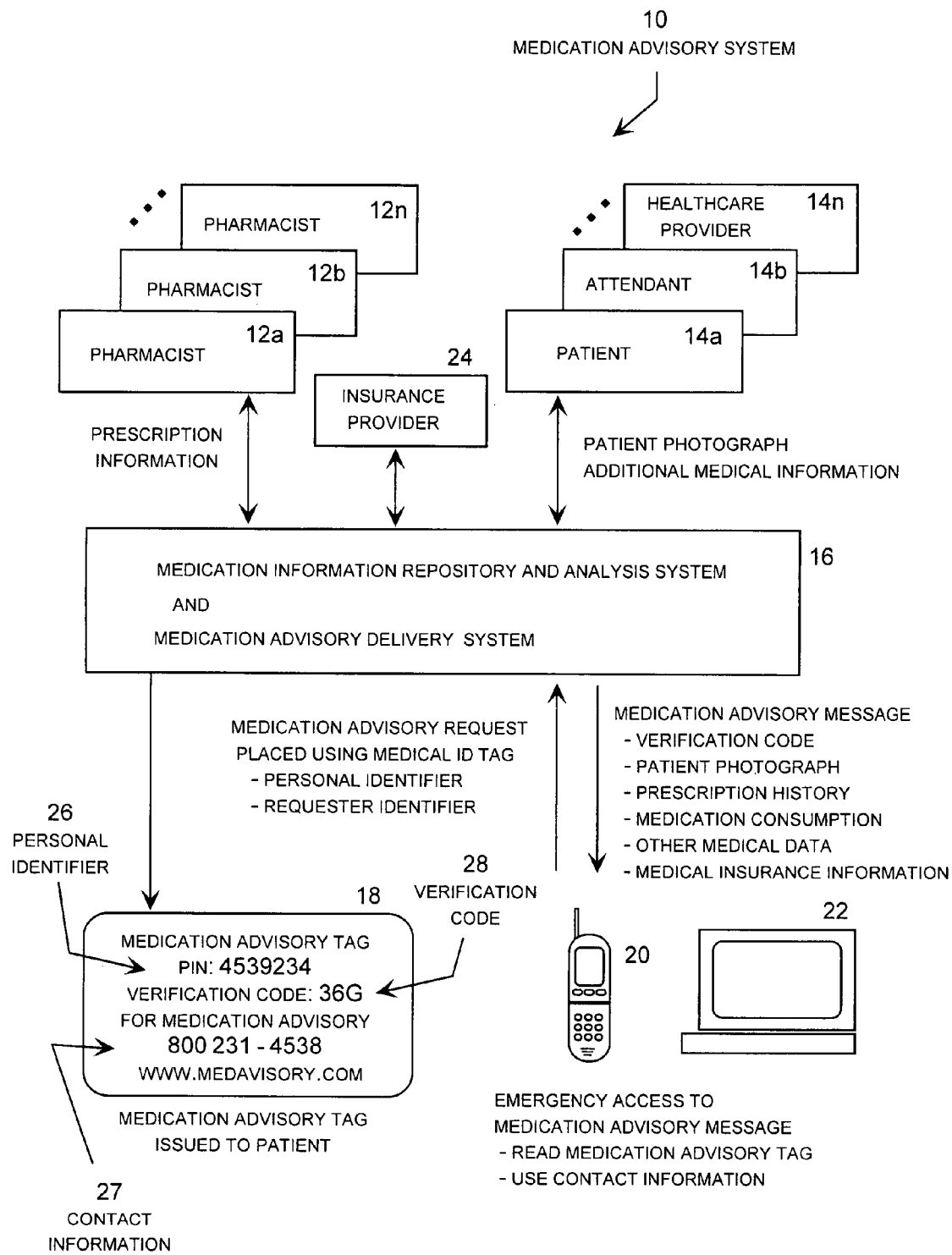
FIG. 1 is a block diagram showing how the medication history is updated by a Pharmacist each time the Patient obtains a new prescription or refills an old prescription. While waiting for the medications, the Patient or Attendant uses a computer device to complete an electronic questionnaire, thereby providing other medical information.

In the following detailed description, for purpose of explanation, specific details are set forth in order to provide an understanding of specific embodiments of the invention. It will be apparent, however, to one skilled in the art that the invention is not limited to these specific embodiments. Further, in the embodiments of the present invention, reference is made to the accompanying figures, which in conjugation with this detailed description, illustrates and describes the novel concepts.

The medication information repository receives medication information from pharmacists and conveys this information to emergency healthcare workers to help them select the best medications and other treatments for their patients. The pharmacists will update the information repository, specifying current medications and dosages each time a patient fills or refills a prescription. This is often important because some patients have no idea what medications they have been taking when they arrive at a treatment center such as a hospital emergency room, and the emergency room staff must treat seriously injured patients very quickly. The pharmacists will be expected to report the prescribed dosage schedule for each medication and will also report the actual consumption rate based on the last two dates that each prescription was refilled, e.g. "actual consumption rate=23 pills/month @ 30 mg/pill." While waiting at the pharmacy for the prescription(s), the patient or attendant will report the latest medical information using a computer or simple questionnaire. The two sets of data will be merged into a repository address linked to the patient's personal identifier, such as a PIN. A person with a clear voice will then record each emergency voice message under the watchful eye of an experienced nurse.

Healthcare workers will be able to use a telephone or cell phone to hear a pre-recorded voice message about the medication and medical history of a patient. The medication details will be also available as a text plus graphics message to the cell phone or as a more detailed text plus graphics message to a computer. There can be three levels of security in accessing the telephone message, i.e. the patient identifier (e.g., patient's PIN), the requester identifier (e.g., emergency worker's PIN), and the pre-approved cell phone number or IP address. The patient's PIN will be printed on the medication advisory tag worn or carried by the patient. The repository computer or human operator will also communicate a verification code to allow the emergency worker to confirm that the information supplied is actually for the patient being treated. The verification code will be also printed on the patient's medical advisory tag.

The repository will report the prescribed dosage schedule for each medication plus the actual consumption rate based on the last two dates of refill. Any future clinician treating the patient will be able to access the repository records and identify the medication and medical history of the patient. Any future clinician treating the patient will be able to access the repository records and identify whether the patient has been forgetting to take prescribed medications. Pharmacists are supposed to know about other medications, recent surgeries, allergies, etc. They are the last checkpoint before a medication error. The described data collection methods will encourage pharmacists to look at these details.

The repository computer or human operator will automatically inform the patient's insurance company, HMO or other identified insurance provider whenever an emergency healthcare worker has requested information from the repository database. The worker's PIN will be used to identify the worker's address and telephone number, which will be reported to the identified insurance provider.

The patients using the system will be issued a medication advisory tag in the form of a card, wearable tab, wearable pendant, bracelet or wristwatch. The medication advisory tag will typically include laser-etched text on a coated metal (e.g. anodized aluminum), laminated plastic or composite material with an RFID tag attached. The wristwatch version of the medical advisory tag will be very useful because it has a battery that could drive an active RFID tag. The PIN and other instructions could be printed on the face or rear surface of the watch. The wristwatch has added significance since the Pharmacies can implement this service and in some cases give the watch away as a promotional item to attract more customers. A free watch could convince an elderly person to wear the medication advisory tag. The RFID tag will be identified by an RFID reader when passing through a hallway or exit door. The proposed laser-etching can produce very small images on a durable anodized aluminum tag. A magnifying lens can be attached to the medical advisory tag for reading the fine print on the tag and for also protecting the fine print on the tag.

The present invention meets the needs described above through a medical history identification tag that contains information for contacting an associated medication records storage system. Pharmacists filling prescriptions for a patient will enter data about the prescriptions into the medication information repository and analysis system. The pharmacists will report the prescribed dosage schedule for each medication and will also report the actual consumption rate based on the last two dates that each prescription was refilled, e.g. "actual consumption rate=23 pills/month @ 30 mg/pill." The medication information repository will contain past and recent information regarding prescriptions filled for the patient. The repository computer will perform an analysis of the patient's prescription refill history to determine medication compliance information for the patient.

While waiting at the pharmacy for the prescription(s), the patient or attendant will report the latest medical information about the patient using a computer or a simple questionnaire. The data compiled by the pharmacist and the patient or attendant will merge into the repository at a computer address linked to the patient's PIN. A repository worker will then transcribe the medication and medical records into a clear and concise voice message. The medication advisory delivery system will store the voice message and other information about the patient as a cell phone text message and as a text plus graphics message for cell phones with graphical displays or for computers. More detailed information will be also provided at a secure website. Healthcare workers will be able to identify current medications and recent medical events, including data that quantifies how often the patient has forgotten to take a prescribed medication.

Long-term details about the patient will be laser-etched on the back of the medication advisory tag, e.g. birth date, diagnosed disabilities, prior surgeries, etc. The medication details will be updated by a pharmacist each time the patient fills or refills a prescription, and the current medication information will be presented in the voice message, text message, and text plus graphics message.

The repository computer or human operator will automatically inform the patient's health insurance company whenever an emergency healthcare worker has requested information from the repository database. The worker's PIN will be used to identify the worker's address and telephone number, which will be reported to the third party payer.

The participating patient or individual will be required to wear or carry a medication advisory tag or card that displays a PIN, verification code and instructions for obtaining the medication and other medical history of the patient or individual. An RFID tag can be attached to the medical advisory tag. When the RFID tag is identified at an exit hallway or door, the binary code on the RFID tag can be used to determine whether the patient or individual is permitted to pass through the hallway or doorway. If egress has been previously denied, an alarm can be triggered to notify staff of the emergency situation.

A difficult problem occurs when an elderly individual forgets or declines to take all of his/her prescribed medications each month; consequently, the prescribed dosages may not be the actual amounts that the patient is consuming. In many cases, the pharmacist is the only professional who knows all of the prescribed medications for the patient. The pharmacists will estimate the average consumption rate for each medication by noting the dates when each prescription was refilled. For all of the above reasons, the medication data in the medication information repository is preferably provided by pharmacists.

Each pharmacy could offer this medication information service free of charge to all customers who bring all of their prescriptions to their pharmacy. The increased so revenue could justify the cost of maintaining the emergency information service. Hence, there is a need and financial incentive for providing the improved medication information system.

Turning now to the figures, in which like numerals refer to like elements throughout the several figures, a particular embodiment of the invention will be described with reference to the figures. Although the medication advisory system can be implemented in a wide variety of ways with many areas of sophistication, the figures show a simple example for the purpose of illustrating the principles of the invention. In practice, many different types of medication advisory systems with different features and levels of sophistication may be implemented, and the features implemented by the systems may vary for different types of vendors and members.

FIG. 1 portrays how information pertaining to a medical patient, typically including personal information, medication information, additional medical information and medical insurance information will be compiled and reported by Pharmacists 12a, 12b, and 12n. While waiting for a prescription (Rx) to be filled, the Patient 14a or Attendant 14b will complete an electronic questionnaire that updates the patient's medical history. The electronic questionnaire will ask the Patient 14a or Attendant 14b about recent surgeries, illnesses, injuries, allergies and other medical details. The electronic questionnaire will be available in different languages. These separate sets of electronic data will be communicated to a Medical Records Repository 16.

A person with a clear voice will record a short voice message based on the Repository Data 16, including medication (Rx) details. The recorded voice message will be accessible by Telephone or Cell Phone 20 to any authorized emergency worker knowing the patient's PIN, which will be listed on the patient's Medical ID Tag 18. To prevent illegal access to the patient's data, the emergency worker must also input a second PIN assigned to the worker or his organization. A third level of security can be added by requiring the call to be made from a previously approved Telephone Number.

Additional medical information will be available to emergency workers, physicians and other pharmacists by using a Computer 22 to directly access the Medical Record Repository 16. Triple security can be implemented by requiring the same two PIN's plus a pre-approved IP Address for the Computer 22 accessing the Repository 16.

It is important to recognize that most elderly patients forget or decline to take all of their prescribed medications each month. In the present invention, medication data will be updated by the patient's pharmacist each time the patient obtains a new prescription or refills an old prescription. The dosage schedule will be reported as both the prescribed rate of consumption (Rx) and the actual rate of consumption, as indicated by the recent refill dates, e.g. Refill Data=23 pills/month at 30 mg/pill. The actual rate of consumption of each medication will be available to the patient's primary care physician(s) via a communication such as a Cell Phone 20, Computer 22, or other suitable device.

The Pharmacist 12a, 12b or 12n is supposed to ask questions about recent surgeries, allergies, diagnoses, etc, but there is usually no efficient method for providing this information to the Pharmacist. While supplying the medication information, the Pharmacist 12a, 12b or 12n will be forced to review the patient's medical history. The Pharmacist 12a, 12b or 12n can also access the Repository 16 using a Computer 22 to obtain medical information about the Patient 14a compiled in the Repository 16 on a prior date.

It is very common for individuals to obtain their medications from more than one Pharmacist, e.g. 12a, 12b and 12n. If the other Pharmacist(s) also report medications details, then each Pharmacist will be better able to evaluate the compatibility of their medications.

If any individual considers their detailed medication information to be an invasion of privacy, then they can decline the medical information service. Celebrities and other well known individuals will be advised to protect their ID Tag or Card 18 since their consumption of medications could be newsworthy and embarrassing.

In the preferred embodiment of the invention, it will not be necessary to print the Patient's name on the ID Tag 18, in the Repository Data 16, or in the communications via Computer 22, Telephone or Cell Phone 20. The Medical ID Tag 18 will have instructions printed or etched onto the Tag 18 explaining how to obtain personal information about the individual via other sources.

The ID Tag 18 will also list a verification code for the Patient 14a. Emergency workers will be instructed via Telephone/Cell Phone 20 and via Computer 22 to compare the communicated verification code with the verification code printed or etched on the Medical ID Tag 18 to verify that the data reported is for the individual being treated. If the verification codes do not match, the worker will be asked to input the PIN again. The Repository 16 can also communicate a photograph of the Patient 14a.

Another important embodiment of the present invention is the fact that the Pharmacist 12a, 12b or 12n will report the medication data as a text message and will not personally record the voice message for each patient. A trained public speaker will record each voice message based on the data provided by the Pharmacist plus additional data obtained from the electronic questionnaire filled out by the Patient 14a or Attendant 14b while waiting for the prescription(s) to be filled or refilled.

When an emergency worker, et al call the telephone number printed or etched on the ID Tag 18, an automatic answering machine or human operator will tell the caller how to access the pre-recorded voice message by inputting the patient's PIN and the caller's PIN. A third level of security can be provided by requiring the caller to use a pre-approved Telephone or Cell Phone 20 number. If the caller passes all of the security checks and if the caller confirms that the communicated verification code matches the verification code on the ID Tag 18, then the Repository 16 computer will play back the pre-recorded voice message. A text message will be also transmitted to the caller's telephone or cell phone, listing each medication, the prescribed consumption rate and the actual consumption rate.

Another important feature of the invention is that each inquiry about the Patient 14a will be reported to the patient's Health Insurance Company, HMO or Veterans Administration (VA) 24 as a FAX, email or telephone message. The emergency worker's PIN will be used to identify the ambulance company or hospital name, telephone number and address that made the inquiry about the Patient 14a, and this information will be included in the report to the third party payer.

Figure 2:
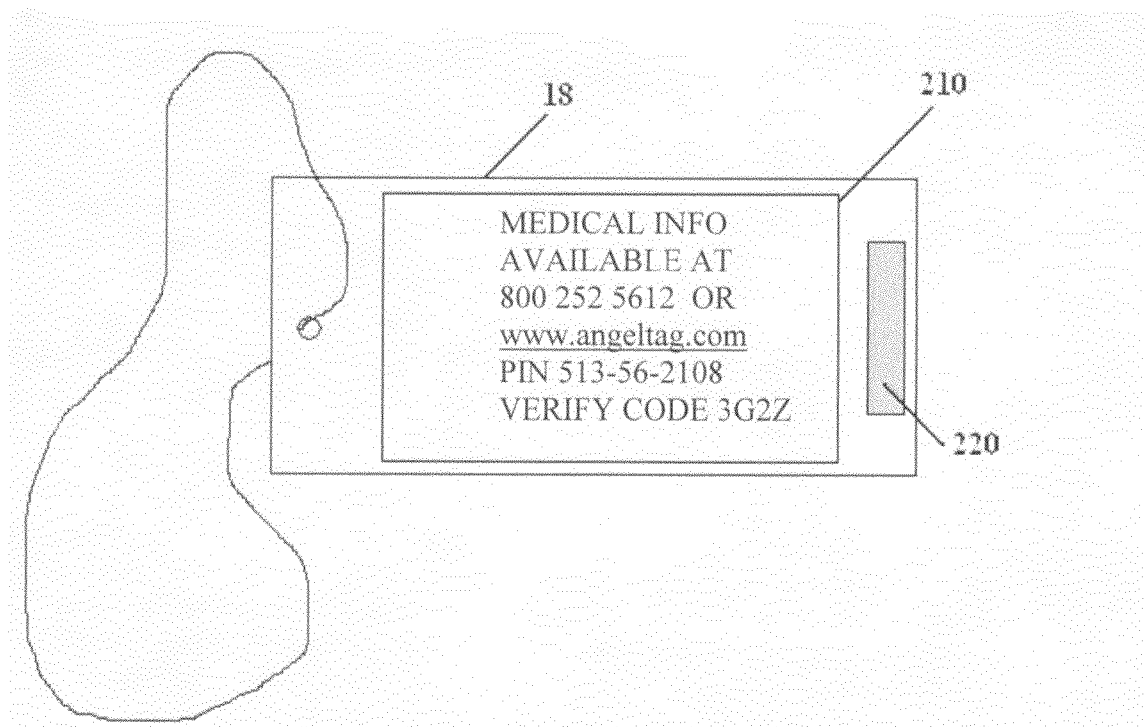
FIG. 2 is a conceptual illustration of a medication advisory tag 18 that can be carried in a wallet like a credit card, worn around the tagged individual's neck like a dog tag, or attached to a keychain. The medication advisory tag displays instructions 210 for obtaining medical information about the patient and may also contains an RFID tag 220.

FIG. 2 illustrates a Medical ID Tag 18 that can be carried in a wallet like a credit card, stuck to the back of a driver's license, worn around the individual's neck like a dog tag, or attached to a garment or key chain. Instructions 210 for obtaining medical information about the tag owner will be printed or etched onto the ID Tag 18. The individual's name and other personal information can be withheld from the Tag 18 and in all other information provided to an emergency worker, et al. A photograph of the Tag Owner can be seen by logging into the Repository 16 using a Computer 22. A Passive RFID Lag 220 can be optionally attached to the front or rear surface of the ID Tag 18.

In the preferred embodiment of the invention, the Medical ID Tag 18 in FIG. 2 is constructed by first polishing a flat piece of aluminum and then anodizing the aluminum in an attractive color. The text can be then created by laser-etching through the anodizing layer. Other coated metals, plastics or composite materials can be used.

Figure 3:
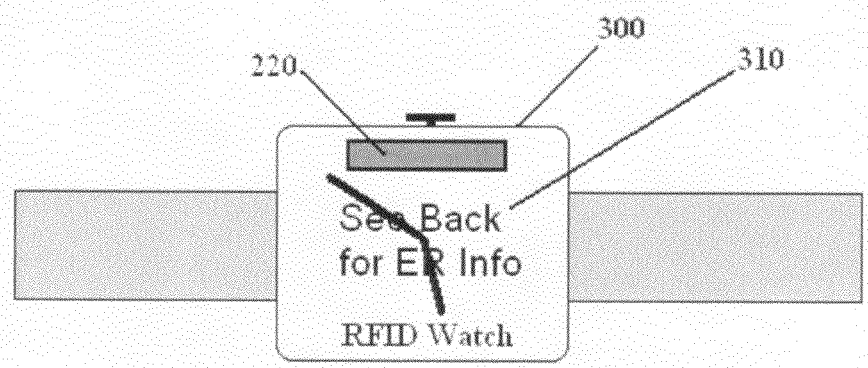
FIG. 3 is a conceptual illustration of a medication advisory tag configured as a wristwatch or bracelet 300 that can be worn on a patent's wrist. The front surface of the medication advisory tag displays instructions 310 for obtaining medical information about the patient and may also contain an RFID tag 220.

FIG. 3 illustrates a medication advisory tag configured as a bracelet or wristwatch 300 with text 310 printed on the face of the watch or bracelet explaining how to obtain emergency information. Pharmacies will be the driving force behind the medical ID service, and one of their incentives will be to attract more customers. A pharmacy could offer the Medical ID service plus a free bracelet or watch 300 to all customers who are willing to bring all of their prescriptions to their pharmacy.

An Active RFID tag 220 and battery could be contained inside the bracelet or wristwatch 300 in FIG. 3. A Passive or Active RFID tag 220 would have particular value for individuals who are under the care of a family member, nursing home or assistive living center and have a history of wandering beyond their prescribed boundaries. When the RFID tag 220 is detected in a hallway or at an exit door by an RFID reader, an alarm could be triggered to alert an attendant that the individual is leaving the building.

Figure 4:
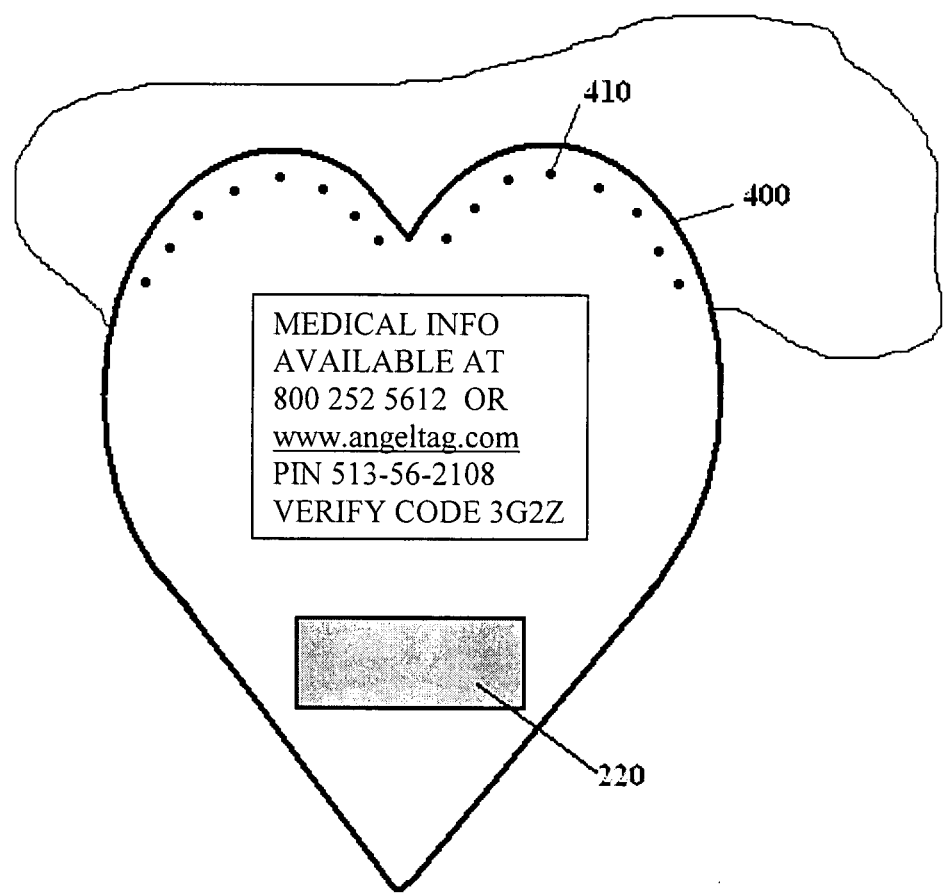
FIG. 4 is a conceptual illustration of a medication advisory tag configured as a jeweled pendant 400. The front or rear surface of the ID Tag displays instructions for obtaining medical information about the Tag owner and may also contain an RFID tag 220.

FIG. 4 presents an example of an ID Tag configured as a jeweled pendant 400, which could be offered by the Pharmacy to female customers. In this example tag, gems 410 are shown along the edge of the pendant. An optional RFID tag 220 can be attached to the front or rear surface of the pendant.

Figure 5A:
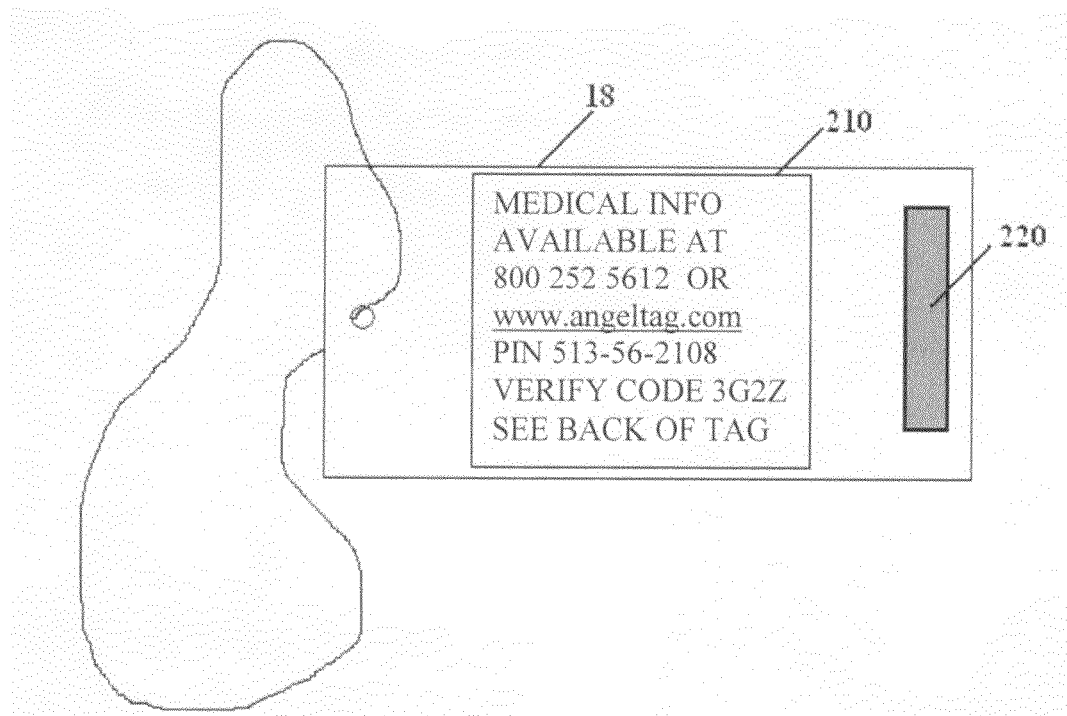
FIG. 5a is a conceptual illustration of a medication advisory tag configured as a dog tag 18 with instructions 210 and an optional RFID tag 220.
Figures 5B, 5C:
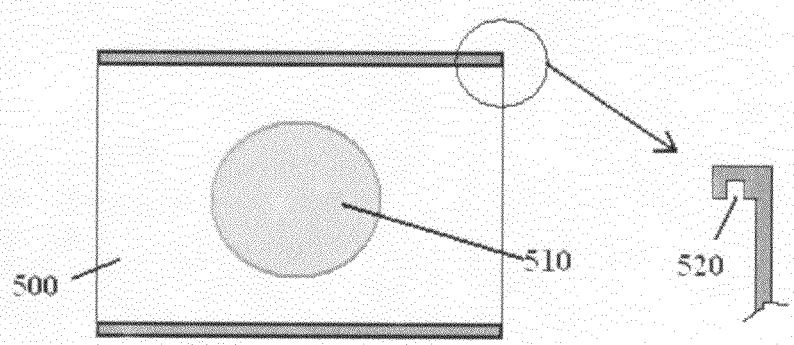
FIG. 5b shows a Protective Cover 500 that slides over or clips onto the medication advisory tag 18. The Protective Cover 500 contains a magnifying lens 510 for reading small print on the Tag.
FIG. 5c illustrates a groove 520 at the top edge of the Protective Cover 500 which is repeated at the bottom edge for holding the Protective Cover 500 against the ID Tag 18.

FIG. 5a presents a modification of the dog tag design with an optional RFID tag on the front or rear surface of the ID Tag 18. FIG. 5b shows a front view of a protective cover 500 that contains a magnifying lens 510. The protective cover 500 slides onto the ID Tag 18 along grooves 520 depicted in FIG.

5c. The magnifying lens can be used to read a small print message printed or etched onto the ID Tag.

Other objects, features and advantages of the invention will be apparent from the drawings, and from the detailed description above. While the present invention has been described with reference to certain exemplary embodiments, those skilled in the art will recognize that various modifications may be provided. Accordingly, the scope of the invention is to be limited only by the following claims. Further, the foregoing description of the invention has been set for merely to illustrate the invention and is not intended to be limiting. Since modifications of the disclosed embodiments incorporating the spirit and substance of the invention may occur to person skilled in the art, the invention should be construed to include everything within the scope of the appended claims and equivalents thereof.

References are made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

The invention claimed is:

1. A medication advisory system for receiving, maintaining and delivering medication information pertaining to a patient, comprising:
   a medication information repository and analysis computer system configured to:
   receive prescription information indicating one or more medication prescriptions filled for the patient and an actual consumption rate based on a plurality of refill dates, analyze the prescription information to determine an estimate of recent medication consumption by the patient, and store a medication advisory message indicating prescription and recent medication consumption information for the patient in association with a personal identifier assigned to the patient;
   a medication advisory delivery computer system configured to automatically deliver the medication advisory message in response to a medication advisory request that is received in accordance with medication advisory contact information and indicates the personal identification number assigned to the patient,
   wherein the medication information repository and analysis computer system and the medication advisory delivery computer system are remotely located from a location associated with the patient; and
   a medication advisory tag configured as a wristwatch, wherein the wristwatch comprises the medication advisory contact information, the personal identifier assigned to the patient, and a RFID tag configured to communicate with an RFID reader positioned at a predetermined location to detect when the patient wearing the wristwatch is in proximity to the predetermined location.

2. The medication advisory system of claim 1, wherein the medication information repository is configured to receive prescription information from multiple pharmacies that have filled prescriptions for the patient and determine the estimate of recent medication consumption by the patient based on the prescription information received form the multiple pharmacies.

3. The medication advisory system of claim 1, wherein the medication advisory system is operative to receive a requester identifier in association with the medication advisory request, and to determine whether the requester identifier is associated with a party authorized to receive the medication advisory message as a condition to delivering the medication advisory message in response to the medication advisory message.

4. The medication advisory system of claim 1, wherein:
   the medication information repository stores a verification code in association with the personal identifier for the patient; and
   the medication advisory message includes the verification code for the purpose of validating that a correct patient identifier has been included in the medication advisory request.

5. The medication advisory system of claim 1, wherein:
   the medication information repository stores a patient photograph in association with the personal identifier for the patient; and
   the medication advisory message includes the patient photograph for the purpose of validating that a correct patient is associated with the medication advisory message.

6. The medication advisory system of claim 1, wherein the medication advisory system comprises a telephone voice response unit, the medication advisory contact information comprises a telephone directory number assigned to the telephone voice response unit, the medication advisory request comprises a telephone call received by the telephone voice response unit, and the medication advisory message comprises a pre-recorded voice message.

7. The medication advisory system of claim 1, wherein the medication advisory system comprises a text message response unit, the medication advisory contact information comprises a text message access number assigned to the text message response unit, the medication advisory request comprises a text message request received by the text message response unit, and the medication advisory message comprises a text plus graphics message response.

8. The medication advisory system of claim 1, wherein the medication advisory system comprises an Internet email server, the medication advisory contact information comprises an Internet address assigned to the Internet email server, the medication advisory request comprises an email received by the Internet email server, and the medication advisory message comprises an automatic email response message sent to an insurance provider associated with the patient, the automatic email response message comprising information associated with the medication advisory request.

9. The medication advisory system of claim 1, wherein the medication information repository is operable for receiving additional medical information pertaining to the patient and including the additional medical information in the medication advisory message.

10. The medication advisory system of claim 1, wherein the additional medical information comprises medication allergy information pertaining to the patient.

11. The medication advisory system of claim 1, where in the medication information repository is operable for receiving medical insurance information pertaining to the patient and including the medical insurance information in the medication advisory message.

12. The medication advisory system of claim 1, wherein the medication advisory delivery computer system is further operative to use the insurance information to deliver a message to an insurance provider notifying the insurance provider that a medication advisory message has been delivered for the patient.

13. A medication advisory system for receiving, maintaining and delivering medication information pertaining to a patient, comprising:

a medication information repository and analysis computer system configured to:

receive prescription information from one or more pharmacists, wherein the prescription information comprises a prescribed dosage of a medication prescribed to the patient, a date that the prescribed dosage was filled, and a date that the prescribed dosage was refilled, and an actual consumption rate based on a plurality of refill dates, analyze the prescription information to determine an estimate of recent medication consumption by the patient, and store a medication advisory message indicating the recent medication consumption of the medication associated with the patient;

a medication advisory delivery computer system configured to:

receive a personal identifier corresponding to the patient from an authorized healthcare provider via a telephone or a cell phone, receive a medication advisory request associated with the patient from the authorized healthcare provider via the telephone or the cell phone, in response to receiving the personal identifier and the medication advisory request, providing the medication advisory message via the telephone or the cell phone, wherein the medication information repository and analysis computer system and the medication advisory delivery computer system are remotely located from a location associated with the patient; and a medication advisory delivery computer system configured to automatically deliver the medication advisory message in response to a medication advisory request that is received in accordance with medication advisory contact information and indicates the personal identification number assigned to the patient, wherein the medication information repository and analysis computer system and the medication advisory delivery computer system are remotely located from a location associated with the patient; and a medication advisory tag configured as a wristwatch, wherein the wristwatch comprises the medication advisory contact information, the personal identifier assigned to the patient and instructions for receiving the medication advisory request via the telephone or the cell phone, and a RFID tag configured to communicate with an RFID reader positioned at a predetermined location to detect when the patient wearing the wristwatch is in proximity to the predetermined location.

14. The medication advisory system of claim 13, wherein:
the medication information repository stores a verification code in association with the personal identifier for the patient; and
the medication advisory message includes the verification code for the purpose of validating that a correct patient identifier has been included in the medication advisory request.

15. The medication advisory system of claim 13, wherein the medication advisory system comprises a text message response unit, the medication advisory contact information comprises a text message access number assigned to the text message response unit, the medication advisory request comprises a text message request received by the text message response unit, and the medication advisory message comprises a text message response.

16. The medication advisory system of claim 13, wherein the medication information repository is operable for receiving additional medical information pertaining to the patient and including the additional medical information in the medication advisory message.

17. The medication advisory system of claim 13, wherein the additional medical information comprises medication allergy information pertaining to the patient.

18. The medication advisory system of claim 13, where in the medication information repository is operable for receiving medical insurance information pertaining to the patient and including the medical insurance information in the medication advisory message.

19. The medication advisory system of claim 13, wherein the medication advisory delivery computer system is further operative to use the insurance information to deliver a message to an insurance provider notifying the insurance provide that a medication advisory message has been delivered for the patient.

20. A method for receiving, maintaining and delivering medication information pertaining to a patient, comprising:

receiving, medication information repository and analysis computer, prescription information indicating one or more medication prescriptions filled for the patient and an actual consumption rate based on a plurality of refill dates;

analyzing, medication information repository and analysis computer, the prescription information to determine an estimate of recent medication consumption by the patient, and storing a medication advisory message indicating prescription and recent medication consumption information for the patient in association with a personal identifier assigned to the patient;

a medication advisory delivery computer system automatically delivering the medication advisory message in response to a medication advisory request that is received in accordance with medication advisory contact information and indicates the personal identification number assigned to the patient, wherein the medication information repository and analysis computer system and the medication advisory delivery computer system are remotely located from a location associated with the patient; and providing a medication advisory tag configured as a wristwatch, wherein the wristwatch comprises the medication advisory contact information, the personal identifier assigned to the patient, and a RFID tag, wherein the RFID tag communicates with an RFID reader positioned at a predetermined location to detect when the patient wearing the wristwatch is in proximity to the predetermined location.

\* \* \* \* \*